United States Patent [19]

Del Rossi et al.

[11] Patent Number: 5,043,503

[45] Date of Patent: Aug. 27, 1991

[54] PRODUCTION OF LUBRICANT STOCKS FROM POLYCYCLIC PARAFFINS

[75] Inventors: Kenneth J. Del Rossi, Mantua; Stuart S. Shih, Cherry Hill, both of N.J.

[73] Assignee: Mobil Oil Corporation, Fairfax, Va.

[21] Appl. No.: 566,927

[22] Filed: Aug. 14, 1990

[51] Int. Cl.$^5$ .............................................. C07C 13/28
[52] U.S. Cl. ...................................... 585/360; 585/375
[58] Field of Search ................................. 585/360, 375

[56] References Cited

U.S. PATENT DOCUMENTS

| | | | |
|---|---|---|---|
| 2,904,607 | 9/1959 | Mattox et al. | 260/671 |
| 3,173,965 | 3/1965 | Pappas et al. | 260/667 |
| 3,251,897 | 5/1966 | Wise | 260/671 |
| 3,382,288 | 5/1968 | Schreider | 585/360 |
| 3,457,318 | 7/1969 | Capaldi et al. | 585/360 |
| 3,751,500 | 8/1973 | Hall | 585/360 |
| 3,792,097 | 12/1974 | Shimada et al. | 585/375 |
| 3,928,480 | 2/1975 | Tabushi et al. | 585/375 |
| 4,035,308 | 7/1977 | Schenach | 252/59 |
| 4,148,834 | 4/1979 | Kennedy et al. | 260/671 |
| 4,691,068 | 9/1987 | Resh | 585/323 |

*Primary Examiner*—Patrick P. Garvin
*Assistant Examiner*—E. D. Irzinski
*Attorney, Agent, or Firm*—Alexander J. McKillop; Charles J. Speciale; Robert B. Furr, Jr.

[57] ABSTRACT

Alkylated polycycloparaffinic compounds useful as lubricating stocks are prepared by alkylating a polycycloparaffinic compound with an alkylating agent under alkylation reaction conditions in the presence of a zeolite catalyst. Useful zeolites include zeolite Beta as well as zeolites having a Constraint Index of from about 1 to about 10, such as ZSM-5 and MCM-22. In a preferred embodiment, the polycycloparaffin comprises adamantane and the alkylating agent is a $C_{14}$ alpha-olefin.

30 Claims, No Drawings

PRODUCTION OF LUBRICANT STOCKS FROM POLYCYCLIC PARAFFINS

FIELD OF THE INVENTION

The present invention relates to a process for the production of lubricant stocks. More specifically, the invention provides a process for the production of low pour point, high Viscosity Index lubricant base stocks by the alkylation of polycyclic paraffins with alpha olefins.

BACKGROUND OF THE INVENTION

This invention relates to a process for alkylating polycyclic paraffins to form lubricating stocks by contacting the polycyclic paraffin with an alkylating agent in the presence of a zeolite alkylation catalyst.

Diamondoid compounds exemplify the polycyclic alkanes useful in the present process. The term "diamondoid" as used herein refers to a family of compounds including adamantane and its higher homologs such as diamantane and triamantane as well as their substituted derivatives.

While diamondoid compounds may be synthesized in the laboratory, the costs associated with laboratory synthesis have in the past precluded consideration of diamondoid compounds such as adamantane as high volume raw materials. Fortunately, however, a naturally occurring deposit of these compounds has recently been discovered in which the diamondoid compounds are dissolved in natural gas. The production of natural gas is complicated by the presence of these heavy hydrocarbons in the subterranean formation in which the gas is found. Under conditions prevailing in the subterranean reservoirs, the heavy hydrocarbons may be partially dissolved in the compressed gas or finely divided in a liquid phase. The decrease in temperature and pressure attendant to the upward flow of gas as it is produced to the surface result in the separation of solid hydrocarbonaceous material from the gas. This solid material has been found to be rich in diamondoid compounds. Unfortunately, however, the deposition of this solid initially caused severe plugging problems both in the natural gas well and in the downstream production string.

Various processes have been developed to prevent the formation of such precipitates or to remove them once they have formed. These include mechanical removal of the deposits and the batchwise or continuous injection of a suitable solvent. Recovery of one such class of heavy hydrocarbons, i.e. diamondoid materials, from natural gas is detailed in commonly assigned.

These natural gas streams contain a small proportion of diamondoid compounds, but their considerable volumetric flow provides a sufficient quantity of diamondoids to consider these materials as industrial feedstocks. For a survey of the chemistry of diamondoid compounds, see Fort, Jr., Raymond C., *The Chemistry of Diamond Molecules*, Marcel Dekker, 1976.

In recent times, new sources of hydrocarbons have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presence of diamondoid compounds in natural gas has been found to cause plugging in the process equipment requiring costly maintenance downtime to remove. On the other hand, these very compounds which can deleteriously affect the profitability of natural gas production are themselves valuable products. Specifically, it has been found that such polycyclic alkanes can be catalytically alkylated with certain olefins in the presence of a zeolite catalyst to form useful lubricating stocks.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Patent No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865; and 4,104,294 describe crystalline silicates of varying alumina and metal content.

Alkylation is one of the most important and useful reactions of hydrocarbons. Lewis and Bronsted acids, including a variety of natural and synthetic zeolites, have been used as catalysts. Alkylation of aromatic hydrocarbon compounds employing certain crystalline zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F., thereby maintaining patentee's preferable operating phase as substantially liquid.

U.S. Pat. No. 2,904,607 shows alkylation of hydrocarbon compounds in the presence of certain crystalline zeolites. The zeolites described for use in this patent are crystalline metallic aluminosilicates, such as, for example, magnesium aluminosilicate.

U.S. Pat. No. 3,173,965 discloses the alkylation of benzene with olefin in the presence of a Friedel-Crafts catalyst, e.g. $AlCl_3$, $AlBr_3$, $FeCl_3$, $SnCl_4$, $BF_3$, $ZnCl_2$, HF, $H_2SO_4$, $P_2O_5$ and $H_3PO_4$, to provide a polyalkylated benzene product of relatively high viscosity index (V.I.), i.e. from 90 to 245, which is useful as a lubricant.

According to U.S. Pat. No. 4,035,308, excess benzene is alkylated with decene dimer in the presence of $BF_3$-promoted anhydrous $AlCl_3$ to provide a monoalkyl benzene product useful as a lubricant or power transmission fluid.

U.S. Pat. No. 4,148,834 describes a two-step alkylation process for preparing di-long chain alkyl aromatic compounds, useful as lubricants, in which aromatic hydrocarbon is alkylated with linear monoolefin in the presence of HF catalyst in a first step and aluminum chloride or aluminum bromide catalyst in a second step.

U.S. Pat. No. 4,691,068 discloses the preparation of long chain monoalkyl aromatics, useful in producing detergents, employing a Friedel-Crafts catalyst, e.g. $AlCl_3$—HCl, and featuring the recycle of a heavy boiling product fraction to the alkylation reaction

SUMMARY OF THE INVENTION

The present invention includes a process for producing lubricant stock having low pour point and high Viscosity Index by alkylating a polycyclic paraffin with an alkylating agent in the presence of a zeolite catalyst. Useful zeolites include zeolite Beta as well as the zeolites having Constraint Indices from about 0.1 to about 10 such as zeolites having the structure of MCM-22 or ZSM-5. MCM-22 is characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms. The present invention provides a process for alkylating diamondoids with $C_4$-$C_{30}$ olefins to produce a lubricant stock. The invention further provides a process for alkylating adamantane with $C_8$-$C_{16}$ alpha-olefins to produce an alkylated polycycloparaffinic lubricant stock having low pour point and high Viscosity Index.

The invention achieves these and other objectives by the steps of contacting at least one alkylatable polycycloparaffinic compound with at least one alkylating agent possessing an alkylating aliphatic group having from 1 to 30 carbon atoms under alkylation reaction conditions and in the presence of a zeolite catalyst to provide an alkylated polycycloparaffinic lubricating stock possessing at least one alkyl group derived from said alkylating agent.

DESCRIPTION OF SPECIFIC EMBODIMENTS

FEEDSTOCKS

The preferred feedstock used in the present invention includes two components: the polycyclic alkane and the olefin alkylating agent. These two components are suitably present in molar ratios of polycyclic alkane:olefin alkylating agent of from about 100:1 to about 1:20, preferably from about 10:1 to about 1:5, and more preferably from about 2:1 to about 1:3.

POLYCYCLIC ALKANES

The polycyclic alkane feedstocks useful in the present invention include the diamondoid compounds such as adamantane, diamantane and triamantane. Alkyl-substituted diamondoid compounds are also useful feedstocks with the limitation that the diamondoid backbone structure must contain at least one readily alkylatable reaction site. Further, the substituent groups surrounding the alkylatable reaction site or sites must be sufficiently small to avoid hindering the alkylation agent's access to the reaction site or sites.

Recovery of diamondoid compounds, one such class of polycyclic alkanes, from natural gas is detailed in commonly assigned U.S. Pat. Nos. 4,952,747, 4,952,748 and 4,952,749, as well as allowed U.S. patent application 358,761, filed May 26, 1989, all of which are incorporated herein by reference. These are cited for the details of recovering diamondoid compounds from a hydrocarbon gas stream having diamondoid compounds dissolved therein.

Both substituted and unsubstituted polycycloparaffinic hydrocarbons can be alkylated in accordance with the present invention. Suitable unsubstituted polycycloparaffinic hydrocarbons include unsubstituted diamondoid compounds such as adamantane, diamantane, and triamantane. Substituted polycycloparaffinic compounds which can be alkylated herein must possess at least one hydrogen atom directly bonded to the polycycloparaffinic nucleus. The polycycloparaffinic rings can be substituted with one or more alkyl, aryl, alkoxy, aryloxy, cycloalkyl, and/or other groups which do not interfere with the alkylation reaction.

Generally the alkyl groups which can be present as substituents on the polycyclic alkane feedstock contain from 1 to about 30 carbon atoms and preferably from about 1 to 10 carbon atoms, and most preferably from about 1 to 5 carbon atoms.

Suitable polycyclic alkane feedstocks include diamondoids such as adamantane, diamantane, and triamantane, as well as bicyclopentyl, bicyclohexyl, decahydronaphthalene, dicyclohexylmethane, perhydrofluorene, perhydroanthracene, dicyclohexylcyclohexane, and dicyclopentylcyclopentane. Higher molecular weight alkylaromatic hydrocarbons can also be used as starting materials and include polycycloparaffinic hydrocarbons such as are produced by the alkylation of polycyclic paraffins with olefin oligomers. Examples of such products include butyl-tetralin, decyl-indan, dodecyl-fluorene, and dodecyl-anthracene.

ALKYLATING AGENTS

The alkylating agents which are useful in the process of this invention generally include any organic compound having at least one available alkylating group capable of reaction with the alkylatable polycycloparaffinic compound, the alkylating group possessing from 1 to 30 carbon atoms, preferably 6 to 20 carbon atoms, and more preferably 4 to 16 carbon atoms. The most preferred alkylating agent is a mixed stream of alpha-olefins having from 10 to 16 carbons atoms. Examples of suitable alkylating agents are olefins such as 1-octene, 1-decene, 1-dodecene, 1-tetradecene, 1-hexadecene, 1-octadecene; alcohols (inclusive of monoalcohols, dialcohols, trialcohols, etc.) such as 1-octanol, 1-dodecanol, 1-decanol, 1-tetradecanol, 1-hexadecanol, 1,4-butanadiol, 1,8-octanediol; and, alkyl halides such as 1-chlorobutane, 1-chlorooctane, 1-chlorotetradecane, 1-bromodecane, and 1-bromohexadecane, merely to name a few.

Mixtures of alpha-olefins are especially useful as alkylating agents in the alkylation process of this invention. Accordingly, mixtures of 1-octene, 1-nonene, 1-decene, 1-undecene, 1-dodecene, 1-tetradecene, 1-pentadecene, 1-hexadecene, and 1-octadecene, are most preferred. For example, a typical mixed alpha-olefin stream preferred for use in the present process possesses the following composition:

| Alpha Olefin | wt. % |
|---|---|
| $C_6$ | 4.0 |
| $C_9$ | 12.0 |
| $C_{12}$ | 35.0 |
| $C_{15}$ | 43.0 |
| $C_{18+}$ | 6.0 |

CATALYSTS

The catalysts useful in the present invention include those catalysts which exhibit Constraint Indices of from about 0.1 to about 10, for example ZSM-5 and MCM-22. Zeolite Beta is also useful in the present invention, although it is well recognized that the Constraint Index of zeolite Beta varies widely with temperature. Zeolite Beta is described in U.S. Pat. No. 4,696,732; 3,308,069, as well as Re. 28,341, the entire contents of which are incorporated by reference as if set forth at length herein.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732, cited above, discloses Constraint Index values for typical zeolite materials and is incorporated by reference as if set forth at length herein for detailed catalyst descriptions and Constraint Index values.

In one embodiment, the catalyst is a zeolite having a Constraint Index of between about 0.1 and about 10. Examples of such zeolite catalysts include ZSM-5, ZSM-12, MCM-22, and zeolite Beta.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-12 and the conventional preparation thereof are described in U.S. Pat. No. 3,832,449, the disclosure of which is incorporated herein by reference.

Catalysts such as ZSM-5 combined with a Group VIII metal described in U.S. Pat. No. 3,856,872, incorporated by reference as if set forth at length herein, are also useful in the present invention.

Additional catalytic materials useful in the present invention include materials which are readily identified by their characteristic X-ray diffraction patterns. In their calcined form, these synthetic porous crystalline material components which may be employed in a catalyst composition useful in the process of this invention are characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, these materials may be characterized by an X-ray diffraction pattern in their calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |

TABLE C-continued

| Interplanar d-Spacing (A) | Relative Intensity, $I/I_o \times 100$ |
| --- | --- |
| 2.82 ± 0.05 | W |
| 2.78 ± 0.05 | W |
| 2.68 ± 0.05 | W |
| 2.59 ± 0.05 | W |

Most specifically, these materials may be characterized in their calcined form by an X-ray diffraction pattern including the following lines:

TABLE D

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20

M=20-40

S=40-60

VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 $m^2/gm$ as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for preparing short chain alkylaromatics. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use as alkylation catalyst, the zeolite crystals should be subjected to thermal treatment to remove part or all of any organic constituent present therein.

The zeolite alkylation catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of cocrystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the alkylation process of this invention, the zeolite crystals should be dehydrated, at least partially. This can be done by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g, aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Patent No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the crystalline material with another material which is resistant to the temperatures and other conditions employed in the alkylation process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that alkylation products can be obtained economically and orderly without employing other means for controlling the rate of reaction. These materials may be incorporated into naturally occurring clays, e.g., bentonite and kaolin. Said materials, i.e., clays, oxides, etc., function as binders for the catalyst. These clay binders have been employed normally only for the purpose of improving the crush strength of the catalyst.

Naturally occurring clays which can be composited with zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the alkylation catalyst of the invention may be increased by steaming. U.S. Pat. Nos. 4,663,492; 4,594,146; 4,522,929; and 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5-100% steam at a temperature of at least about 300° C. (e.g., 300-650° C.) for at least one hour (e.g., 1-200 hours) at a pressure of 101-2,500 kPa. In a more particular embodiment, the catalyst can be made to undergo steaming with 75-100% steam at 315-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

Alkylation of an alkylatable polycycloparaffinic compound in accordance with the invention is effected by contact of the reactants at a temperature of between about 0° C. and about 500° C., and preferably between about 50° C. and about 250° C. The reaction generally takes place at pressures of from about 0.2 to about 250 atmospheres and preferably from about 1 to about 25 atmospheres. The molar ratio of alkylatable polycycloparaffinic compound to alkylating agent can be from about 100:1 to about 1:20, and preferably can be from about 2:1 to about 1:3. Reaction is suitably accomplished utilizing a feed weight hourly space velocity (WHSV) of between about 0.1 hr$^{-1}$ and about 500 hr$^{-1}$ and preferably from 0.5 hr$^{-1}$ to about 100 hr$^{-1}$. The latter WHSV is based upon the total weight of active catalyst (and binder if present).

The alkylation process of this invention can be carried out as a batch-type, semi-continuous or continuous operation utilizing a fixed, fluidized or moving bed catalyst system.

In order to more fully illustrate the alkylation process of this invention and the manner of practicing same, the following examples are presented. In the examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The following Examples 1-14 show synthesis and characterization of a catalytic material useful in the present invention, which is commonly referred to as MCM-22.

EXAMPLE 1

One part of sodium aluminate (43.5%, Al$_2$O$_3$, 32.2% Na$_2$O, 25.6% H$_2$O) was dissolved in a solution containing 1 part of 50% NaOH solution and 103.13 parts H$_2$O. To this was added 4.50 parts hexamethyleneimine. The resulting solution was added to 8.55 parts of Ultrasil, a precipitated, spray-dried silica (about 90% SiO$_2$).

The reaction mixture had the following composition, in mole ratios:
SiO$_2$/Al$_2$O$_3$=30.0
OH$^-$/SiO$_2$=0.18
H$_2$O/SiO$_2$=44.9
Na/SiO$_2$=0.18
R/SiO$_2$=0.35
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:
H$_2$O: 15.2 wt. %

Cyclohexane: 14.6 wt. %
n-Hexane: 16.7 wt. %

The surface area of the calcined crystalline material was measured to be 494 m²/g.

The chemical composition of the uncalcined material was determined to be as follows:

| Component | wt. % |
| --- | --- |
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE E

| Degrees 2-Theta | Interplanar d-Spacing (A) | $I/I_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLE 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
| --- | --- | --- | --- |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, m²/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product as water washed and dried at 120° C.

Product chemical composition (uncalcined), surface area and adsorption analyses results were as set forth in Table G:

TABLE G

| Product Composition | |
| --- | --- |
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, m²/g | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite has very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

$H_2O$ (12 Torr): 11.7 wt. %
Cyclohexane (40 Torr): 7.5 wt. %
n-Hexane (40 Torr): 11.4 wt. %

The surface area of the calcined crystalline material was measured (BET) to be 405 $m^2/g$.

The chemical composition of the uncalcined material was determined to be as follows:

N: 1.94 wt. %
Na: 175 ppm
K: 0.60 wt. %
Boron: 1.04 wt. %
$Al_2O_3$: 920 ppm
$SiO_2$: 75.9 wt. %
Ash: 74.11 wt. %
$SiO_2/Al_2O_3$, molar ratio = 1406
$SiO_2/(Al+B)_2O_3$, molar ratio = 25.8

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2/B_2O_3 = 12.3$
$OH^-/SiO_2 = 0.056$
$H_2O/SiO_2 = 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

$H_2O$ (12 Torr): 14.4 wt. %
Cyclohexane (40 Torr): 4.6 wt. %
n-Hexane (40 Torr): 14.0 wt. %

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

Zeolite MCM-22 was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried.

A portion of the zeolite crystals was combined with $Al_2O_3$ to form a mixture of 65 parts, by weight, zeolite and 35 parts $Al_2O_3$. Water was added to this mixture to allow the resulting catalyst to be formed into extrudates. The catalyst was activated by calcining in nitrogen at 540° C. (1000° F.), followed by aqueous ammonium nitrate exchange and calcining in air at 540° C. (1000° F.).

EXAMPLE 16

To demonstrate the alkylation of a polycyclic alkane to form a useful lubricant stock, adamantane was alkylated with a $C_{14}$ alpha-olefin. For comparison, the $C_{14}$ alpha-olefin was also reacted in the absence of adamantane under identical conditions. Ten (10) grams of pure MCM-22 powder synthesized in accordance with Example 1 above were loaded in a 1 liter stainless steel autoclave. A 2:1 mole/mole mixture of a $C_{14}$ alpha-olefin and adamantane was then added to the autoclave, and reacted at 290° F. and 300 psig. The mixture was vigorously stirred during the reaction. After 15 hours, the autoclave was cooled, and the liquid product was collected and weighted. The liquid was distilled under atmospheric pressure and the 650° F.+ fraction was weighed and analyzed. The results of the adamantane alkylation run and the $C_{14}$ alpha-olefin run are compared below in Table H.

TABLE H

| | Adamantane alkylation with $C_{14}$ alpha-olefin | $C_{14}$ alpha-olefin feed alone |
|---|---|---|
| Conditions | | |
| MCM-22 catalyst, g | 10 | 10 |
| Adamantane, g | 71 | 0 |
| $C_{14}$ olefin, g | 213 | 150 |
| Temperature, °F. | 290 | 290 |
| Hours | 15 | 15 |
| Conversion, wt. % | | |
| Based on Adamantane Feed | 83 | — |
| Based on Olefin | 62 | 27 |

| Comparison of Properties: Adamantane Feed vs. 650° F.+ Alkylated Product | 650° F.+ Alkylated Adamantane Product | $C_{14}$ = Product Properties |
|---|---|---|
| Pour Point, °F. | −15 | −60 |
| Bromine Number | 22.6 | 42.1 |
| KV at 40° C., cs | 30.49 | 12.83 |
| KV at 100° C., cs | 5.703 | 3.208 |
| SUS at 100° F., sec. | 156.5 | 72.8 |
| SUS at 212° F., sec. | 45.3 | 37.1 |
| Viscosity Index | 130 | 116.2 |

| Distillation, °F. | 650° F.+ Alkylated Product | $C_{14}$ = Product |
|---|---|---|
| IBP | 534 | 556 |
| 5% | 725 | 733 |
| 10% | 734 | 741 |
| 30% | 753 | 755 |
| 50% | 778 | 769 |
| 70% | 909 | 778 |
| 90% | 954 | 794 |
| 95% | 1036 | 897 |
| EP | 1116 | 1012 |

EXAMPLE 17

The procedure of Example 16 was repeated with decahydronaphthalene (formula: $C_{10}H_{18}$) and a second sample of the $C_{14}$ alpha-olefin used in Example 15. The mixture was reacted at 350° F. and 300 psig for 15 hours, after which the autoclave was cooled, and the liquid product was collected and weighed. The liquid was distilled under atmospheric pressure and the 650° F.+ fraction was weighed and analyzed. The results are shown below in Table I.

TABLE I

| | Adamantane alkylation with $C_{14}$ alpha-olefin | $C_{14}$ alpha-olefin feed alone |
|---|---|---|
| Conditions | | |
| MCM-22 catalyst, g | 10 | 10 |
| Decahydro-naphthalene, g | 80 | 0 |
| $C_{14}$ olefin, g | 220 | 150 |
| Temperature, °F. | 350 | 290 |
| Hours | 15 | 15 |
| Conversion, wt. % | | |
| Based on Decahydro-naphthalene feed | 6.2 | — |
| Based on Olefin | 44 | 27 |

| Comparison of Properties: Decahydro-naphthalene Feed vs. 650° F.+ Alkylated Product | 650° F.+ Alkylated Product | $C_{14}$ Product |
|---|---|---|
| Pour Point, °F. | −60 | −60 |
| Bromine Number | 49.5 | 42.1 |
| KV at 40° C., cs | 16.50 | 12.83 |
| KV at 100° C., cs | 3.72 | 3.208 |
| SUS at 100° F., sec. | 88.9 | 72.8 |
| SUS at 212° F., sec. | 38.8 | 37.1 |
| Viscosity Index | 113.2 | 116.2 |
| Distillation, °F. | | |
| IBP | 604 | 556 |
| 5% | 706 | 733 |
| 10% | 724 | 741 |
| 30% | 743 | 755 |
| 50% | 749 | 769 |
| 70% | 757 | 778 |
| 90% | 776 | 794 |
| 95% | 931 | 897 |
| EP | 1034 | 1012 |

Changes and modifications in the specifically described embodiments can be carried out without departing from the scope of the invention which is intended to be limited only by the scope of the appended claims.

What is claimed is:

1. A process for preparing alkyl polycycloparaffinic compounds which comprises contacting at least one alkylatable polycycloparaffinic compound with at least one alkylating agent possessing an aliphatic group having from about 1 to about 30 carbon atoms under alkylation reaction conditions and in the presence of an alkylation catalyst to provide an alkylated polycycloparaffinic product possessing at least one alkyl group derived from said alkylating agent, said catalyst comprising a synthetic porous crystalline material characterized by an X-ray diffraction pattern including values substantially as set forth in Table A of the specification.

2. The process of claim 1 wherein the synthetic porous crystalline material is characterized by an X-ray diffraction pattern including values substantially as set forth in Table B of the specification.

3. The process of claim 1 wherein the synthetic porous crystalline material is characterized by an X-ray diffraction pattern including values substantially as set forth in Table C of the specification.

4. The process of claim 1 wherein the synthetic porous crystalline material is characterized by an X-ray diffraction pattern including values substantially as set forth in Table D of the specification.

5. The process of claim 1 wherein the synthetic porous crystalline material has a composition comprising the molar relationship $$X_2O_3:(n)YO_2,$$

wherein n is at least about 10, X is a trivalent element and Y is a tetravalent element.

6. The process of claim 2 wherein the synthetic porous crystalline material has a composition comprising the molar relationship:

$$X_2O_3:(n)YO_2,$$

wherein n is at least about 10, X is a trivalent element and Y is a tetravalent element.

7. The process of claim 3 wherein the synthetic porous crystalline material has a composition comprising the molar relationship $$X_2O_3:(n)YO_2,$$

wherein n is at least 10, X is a trivalent element and Y is a tetravalent element.

8. The process of claim 4 wherein the synthetic porous crystalline material has a composition comprising the molar relationship $$X_2O_3:(n)YO_2,$$

wherein n is at least about 10, X is a trivalent element and Y is a tetravalent element.

9. The process of claim 1 wherein the synthetic porous crystalline material possesses equilibrium adsorption capacities of greater than about 4.5 wt. % for cyclohexane vapor and greater than about 10 wt. % for n-hexane vapor.

10. The process of claim 5 wherein X is selected from the group consisting of aluminum, boron, gallium and combinations thereof and Y is selected from the group consisting of silicon, germanium and combinations thereof.

11. The process of claim 5 wherein X comprises aluminum and Y comprises silicon.

12. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

13. The process of claim 1 wherein synthetic porous crystalline material has been thermally treated at a temperature up to about 925° C. in the presence of absence of steam.

14. The process of claim 12 wherein said synthetic porous crystalline material has been thermally treated at a temperature up to about 925° C. in the presence or absence of steam.

15. The process of claim 1 wherein said synthetic porous crystalline material is combined with a matrix material.

16. The process of claim 15 wherein said matrix material is a silica- or alumina-containing material.

17. The process of claim 15 wherein said matrix material is a zirconia- or titania-containing material.

18. The process of claim 15 wherein the catalyst is provided in the form of extrudate, beads or fluidizable microspheres.

19. The process of claim 1 wherein the alkylating agent is an alpha-olefin of from 4 to 30 carbon atoms.

20. The process of claim 1 wherein the alkylating agent is an alcohol or halide containing from about 4 to about 30 carbon atoms 21. The process of claim 1 wherein the alkylatable polycycloparaffinic compound is a diamondoid compound.

22. The process of claim 21 wherein the alkylatable polycycloparaffinic compound is selected from the group consisting of adamantane, diamantane, triamantane and substituted homologs thereof.

23. The process of claim 1 wherein the alkylatable polycycloparaffinic compound is adamantane and the alkylating agent is an alpha-olefin having from about 8 to about 16 carbon atoms.

24. The process of claim 1 wherein the alkylation reaction conditions include a temperature of between about 0° C. and about 500° C., a pressure of from about 0.2 to about 250 atmospheres, a WHSV of from about 0.1 to about 500 and a molar ratio of alkylatable polycycloparaffinic compound to alkylating agent of from about 0.1:2 to about 100:1.

25. The process of claim 1 wherein the alkylation reaction conditions include a temperature of between about 50° C. to about 250° C., a pressure of from about 1 to about 25 atmospheres, a WHSV of from about 0.5 to about 100 and a molar ratio of alkylatable polycycloparaffinic compound to alkylating agent of from about 2:1 to about 1:3.

26. A process for alkylating a polycycloparaffinic hydrocarbon comprising at least one selected from the group consisting of adamantane, diamantane, triamantane and the substituted homologs thereof which comprises contacting the alkylatable polycycloparaffinic hydrocarbon with an alpha-olefinic alkylating agent having from 4 to 30 carbon atoms under alkylation reaction conditions and in the presence of an alkylation catalyst selected from the group consisting of a synthetic porous crystalline material characterized by an X-ray diffraction pattern including values substantially as set forth in Table A of the specification.

27. The process of claim 26 wherein the polycycloparaffinic hydrocarbon contains at least one alkyl substituted group.

28. A process for preparing alkyl polycycloparaffinic compounds which comprises contacting at least one alkylatable polycycloparaffinic compound with at least one alkylating agent possessing an aliphatic group having from about 4 to about 30 carbon atoms under alkylation reaction conditions and in the presence of an alkylation catalyst to provide an alkylated polycycloparaffinic product possessing at least one alkyl group derived from said alkylating agent, said catalyst comprising a synthetic porous crystalline material having a Constraint Index of from about 0.1 to about 10.

29. The process of claim 28 wherein said synthetic porous crystalline material has the structure of at least one selected from the group consisting of ZSM-5, ZSM-12, zeolite beta, mordenite, ZSM-4 and zeolite Y.

30. A process for preparing alkyl polycycloparaffinic compounds which comprises contacting at least one alkylatable polycycloparaffinic compound with at least one alkylating agent possessing an aliphatic group having from about 4 to about 30 carbon atoms under alkylation reaction conditions and in the presence of an alkylation catalyst to provide an alkylated polycycloparaffinic product possessing at least one alkyl group derived from said alkylating agent, said catalyst comprising a synthetic porous crystalline material having the structure of zeolite Beta.

* * * * *